United States Patent
Bangert (10) Patent No.: US 8,557,608 B2
(45) Date of Patent: Oct. 15, 2013

(54) METHOD FOR CHARACTERIZING A LOCAL MAGNETIC FIELD, AND DEVICE FOR CARRYING OUT THE METHOD

(75) Inventor: Joachim Bangert, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1881 days.

(21) Appl. No.: 11/603,034

(22) Filed: Nov. 22, 2006

(65) Prior Publication Data

US 2007/0269905 A1 Nov. 22, 2007

(30) Foreign Application Priority Data

Nov. 25, 2005 (DE) .......................... 10 2005 056 249

(51) Int. Cl.
*G01N 33/553* (2006.01)
*G01N 27/00* (2006.01)

(52) U.S. Cl.
USPC ........... 436/526; 436/149; 436/525; 324/214; 324/219; 324/228

(58) Field of Classification Search
USPC ......................................................... 435/6.1
See application file for complete search history.

(56) References Cited

U.S. PATENT DOCUMENTS

2008/0309329 A1* 12/2008 Kahlman et al. .............. 324/228

OTHER PUBLICATIONS

R.L.Edelstein et al.: "The BARC biosensor applied to the detection of biological warfare agents", Biosensors Bioelectronics 14 (2000), p. 805-8513.
G.H.Smith et al.: "High-resolution giant magnetoresistance on-chip arrays for magnetic imaging", Journal of Applied Physics, vol. 93, No. 10, May 15, 2003, p. 6864-6866.
H. Brückl et al.: "Magnetoresistive logic and biochip", Journal of Magnetism and Magnetic Materials, vol. 282, Nov. 2004, p. 219-224.
G. Reiss et al.: "New materials and applications for magnetic tunnel junctions", Phys. Stat. Sol. (a) 201, No. 8, 2004, p. 1628-1634.
German Office Action dated Jun. 12, 2006.
G. Reiss et al., "Magnetoresistive sensors and magnetic nanoparticles for biotechnology", J. Mater. Res., vol. 20, No. 12, Dec. 2005, pp. 3294-3302; Others.

* cited by examiner

*Primary Examiner* — Yelena G Gakh
(74) *Attorney, Agent, or Firm* — Harness, Dickey & Pierce P.L.C.

(57) ABSTRACT

A method is disclosed for characterizing a local magnetic field, in particular a stray field caused by a magnetizable or magnetic particle in a prescribed measuring area of a magnetic field. In at least one embodiment, a sensor array including a number of magnetic sensors and each having at least one layer sensitive to magnetic fields is arranged at least in a subregion of the measuring area, and at least one device is provided for reading out separately the signal from each sensor. According to at least one embodiment, the size, in particular of XMR sensors and the surface of the layer sensitive to magnetic fields and the grid dimension of the sensor array, are selected such that at least two neighboring sensors are influenced by the local stray field. An associated device for carrying out the method is also disclosed.

32 Claims, 4 Drawing Sheets

METHOD FOR CHARACTERIZING A LOCAL MAGNETIC FIELD, AND DEVICE FOR CARRYING OUT THE METHOD

PRIORITY STATEMENT

The present application hereby claims priority under 35 U.S.C. §119 on German patent application number DE 10 2005 056 249.3 filed Nov. 25, 2005, the entire contents of which is hereby incorporated herein by reference.

FIELD

Embodiments of the invention generally relate to a method for characterizing a local magnetic field, in particular a stray field caused by a magnetizable or magnetic particle. In addition, embodiments of the invention also generally relate to a device for carrying out the method.

BACKGROUND

Increasing use is being made in biological analysis technology, medical technology and other comparable fields, of magnetic or magnetizable microparticles with sizes of less than 2 μm, for example as markers or labels for biomolecules. The problem arises in this case of detecting such-particles with the aid of magnetic field sensors. To this end, it is customary to apply an external magnetic field to which the particles react with a magnetic stray field that is to be detected.

It is known with biochips to detect magnetizable particles, which are also denoted as magnetic beads or beads, for short, with the aid of a sensor array that is arranged in the region of an analytical surface of the biochip and is formed from a number of XMR sensors. Because of the size of the individual sensors and their interconnection, it has so far been impossible to make statements on the position of a particle relative to a sensor and on the exact number of particles present in a specific area, and thereby, for example, to infer the number of molecules marked thereby.

A complex system for detecting specific biological structures is known from the publication Biosensor & Bioelectronics 14 (2000), pages 805 to 813. Use is made in this case of a matrix with n GMR sensors that are intended to detect the presence of biologically activated magnetizable particles. The matrix includes 8 arrays with 8 GMR sensors each. The individual sensors are 5 μm wide and 80 μm long. The spacing between the sensors is approximately 20 μm (grid dimension). The particles used have a diameter of 0.7 μm. The aim with this geometry is, in particular, to prevent crosstalk between individual sensors.

The influence of a particle stray field on the sensor resistance is a function of the position of the bead: in the ideal case, the field is entirely covered, whereas the field decreases rapidly at the edge of the sensor. However, the stray field cannot influence more than one sensor, otherwise, for example, an element could not display a zero signal while the neighboring ones indicate half the signal or the whole one. There is no further explanation here of an electronic system suitable for sensor evaluation.

Furthermore, the production of GMR sensor arrays is described in the Journal of Applied Physics, Vol. 93, 10, pages 6864 to 6866. The arrays have 32 or 128 elements and include sub-arrays. The spacing between the sensors is much greater than the dimensions of the sensors. The electronic system reads out the sensors in pairs (half bridge). The sensors have dimensions of 1.5 to 2 μm width and 6 μm length or 32 μm width and 2 mm length. The spacings are 5 μm or 15 μm for the narrow sensors (FIG. 1, FIG. 2) and approximately 200 μm for the wide sensors (FIG. 3). The measuring location resolution of the arrays was determined as approximately 1 mm with the aid of a structure of large area, for example by means of an ink distribution. However, there is in this case no measurement of magnetic or magnetizable microparticles. Further applications named there in addition to biotechnology are nondestructive testing technology, document testing for bank bills or credit cards, for example, or the field of position sensors.

The problem of determining the position of particles relative to the sensors and/or determining the exact number of particles in a specific area is also important for other sets of magnetic questions. In addition to the marking of objects (for example dusts, biological cells), there can also be the need to characterize magnetic microparticles directly, for example when analyzing corrosion products in oils.

SUMMARY

In at least one embodiment of the invention, an improved method is proposed to the effect that statements relating to the position and number of markers located in a measuring area are possible. In addition, a device is to be provided with the aid of which the method can be executed and the field distribution can be determined, the aim also being to specify suitable uses.

It is provided in the case of at least one embodiment of the inventive method that in order to characterize a local stray field caused by a magnetizable or magnetic particle in a prescribed measuring area of a magnetic field, a sensor array composed of a number of XMR sensors each having at least one layer sensitive to magnetic fields is arranged at least in a subregion of the measuring area, and devices/mechanisms/modules are provided for reading out separately the signal from each sensor, the size of the XMR sensors the surface of the layer sensitive to magnetic fields and the grid dimension of the sensor array being selected such that at least two neighboring sensors are influenced by the local stray field. In this case, so-called XMR sensors, in particular GMR or TMR sensors, and ferro-, ferri or antiferromagnetic layer systems are preferably used. Also possible in this context are amorphous layers with appropriate properties sensitive to magnetic fields.

At least one embodiment of the invention assumes that, if each magnetic field sensor can be read out separately independently of other sensor signals, it is certainly possible in principle to detect a single particle present in the region of a sensor. However, this is not yet a sufficient condition for being able to distinguish a single particle from a cluster of a number of particles, for example, or for determining the exact position of a particle in the measuring area. This is first rendered possible according to the invention owing to the fact that the size and grid dimension of the sensors are selected such that the stray field emanating from a particle can be measured at at least two different positions.

The stray field of a particle having approximately a spherical shape, for example, is inhomogeneous, that is to say it has regions of different field strength. Thus, the stray field weakens with increasing distance from the particle surface. Depending on the geometry and alignment of the external magnetic field, field weakenings and field strengthenings occur at different spatial positions.

For example, in the case of an external magnetic field aligned parallel to the flat plane of a sensor array, a field weakening occurs in the region, located between a sensor and the particle, in relation to the external magnetic field, and a field strengthening occurs in the regions located in front of and behind the particle when seen in the direction of the external magnetic field. If, for example, one sensor now detects a field strengthening and another sensor detects a field weakening, it is then possible by comparing the corresponding sensor signals to determine the-position of the particle relatively accurately in relation to a sensor located in the range of influence of the stray field, and to detect a cluster formation.

Furthermore, at least one embodiment of an inventive method can be used to detect particles of the type being discussed with an increased sensitivity. A sensor influenced virtually by the entire stray field integrates the different field strengths to form a total signal, the result being a leveling of the signal when strengthened and weakened stray field regions strike the sensor. In the case of at least one embodiment of an inventive method, by contrast, a smaller stray field region acts on a sensor, so that the leveling effect mentioned occurs at most to a substantially reduced extent.

The measuring, sensitivity is also improved by virtue of the fact that the entire sensor surface is influenced by the stray field of a particle, whereas uninfluenced surface regions are therefore not present, as is the case with sensors whose surface is greater than a particle.

Depending on the size of the individual sensors and the selected grid dimension, the resolution can be freely selected in wide ranges depending on the application. Thus, it is possible to detect in accurate detail locally very narrowly limited changes in the magnetic field. The beads used for biological analyses have a size of approximately 0.5 µm to 2 µm.

It is therefore expedient when the size, for example the diameter or the length and the width, of an XMR sensor is smaller than 2 µm. Sensor arrays with such sensors and correspondingly slight spaces between the sensors can be produced on an industrial scale, for example, with the aid of techniques known from the memory chip industry. In particular consideration is to be given here to techniques for producing magnetic memories, so-called TRAMs (=tunnel magnetoresistive random access memories). According to the invention, such components are, however, not used as data memories, but to characterize magnetic fields.

In at least one embodiment, an inventive device includes a sensor array composed of a number of XMR sensors that in each case have at least one ferromagnetic layer and are interconnected with means for reading out sensor signals such that the signal of each sensor can be read out independently of other sensors, in which the size of the XMR sensors and the surface of the ferromagnetic layer and the grid dimension of the sensor array are selected such that at least two neighboring sensors can be influenced by the local stray field. What has been said above holds by analogy with regard to the advantages attained thereby.

The surface of the XMR sensors and the mutual spacing of neighboring sensors is preferably smaller than 2 µm. This delivers a large multiplicity of applications in the field of microanalysis, in which particles and beads with diameters from approximately 2 µm to 0.5 µm are used.

BRIEF DESCRIPTION OF THE DRAWINGS

Further details and advantages of the invention emerge from the following description of the figures and example embodiments with the aid of the drawings.

In the drawings.

DETAILED DESCRIPTION OF THE EXAMPLE EMBODIMENTS

The first step below is to consider the prior art in order thereupon to explain the novel simulation and computing method for determining a particle occupancy on a sensor arrangement, and to explain the associated devices:

In detail, the aim is measuring arrays or matrices for biomedical purposes with the aid of which, for example, it is possible to perform a DNA and/or a protein analysis. General magnetic measurements for technical applications are also possible.

The measuring matrix used here specifies a setup of identical magnetic field sensors in a given way, and can be of linear or two-dimensional design. In the latter case, a matrix is formed with elements in a prescribed arrangement which is not necessarily symmetrical.

Figure 1:
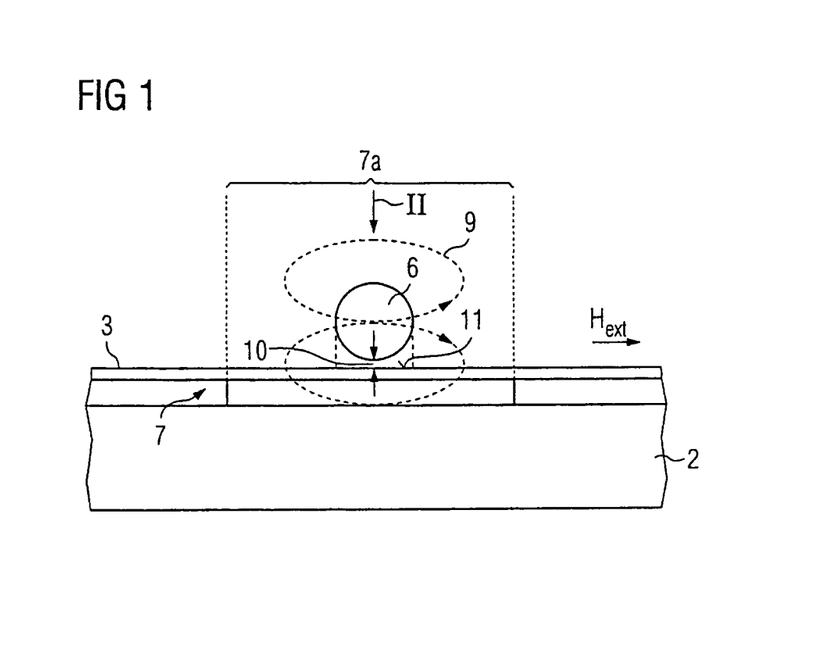
FIG. 1 shows a segment of a biochip in a schematic cross sectional illustration.

A conventional method and a detector for determining a magnetic field gradient are explained by way of example of a biochip 1 that is shown schematically as a section in FIG. 1.

The biochip 1 includes a carrier 2, for example made from $Si_3N_4$. An analytical surface 3 that serves for carrying out analytical reactions is defined on the carrier 2.

A number of such analytical surfaces can be present on a single biochip 1, in particular in the form of an array. A sensor array 7 made from a multiplicity of individual XMR sensors $5_i$ is formed in the carrier 2 below the analytical surface 3.

XMR sensors are based on magnetoresistive effects in magnetic substances. In particular, use is made for this purpose of so-called GMR or TMR sensors: specifically, there is present in the case of GMR sensors (Giant magnetoresistive sensors) a layer system having at least two layers sensitive to magnetic fields and a nonmagnetic, metallic intermediate layer which have ferro-, ferri- or antiferromagnetic properties. Amorphous short range order structures with are also possible.

Particularly in the case of a ferromagnetic system, one layer has a fixed orientation of its magnetic field, while the direction of magnetization of the other layer can be rotated by applying an external magnetic field. Resistance is greater in the case of an antiparallel alignment of the magnetizations than in that of a parallel alignment. There arises a similar situation for TMR sensors (tunnel magneto resistive sensors). A thin insulation layer is present between at least two ferromagnetic layers, the tunnel resistance thereof being a function of the mutual rotary position of the two directions of magnetization.

Magnetizable particles 6, which are also denoted as magnetic beads or beads, for short, are used in the case of an analysis carried out with the aid of a biochip 1 in accordance with FIG. 1. The beads 6 consist, for example, of a styrene matrix incorporating a supermagnetic magnetite material at a proportion of 20%, for example. It is also conceivable to use permanent magnetic materials such as NdFeB and/or demagnetized materials such as pure iron.

Looking for the presence of specific DNA sequences is a typical problem in the field of DNA diagnostics in biotechnology. After diverse preparatory steps—including the propagation of the target DNA sequences—the latter are fixed or immobilized on the analytical surface 3 by means of known methods. Added to the analytical surface 3 is an analyte solution that includes synthetic DNA sequences complementary to the target DNA sequence. The synthetic complements are biotinized, that is to say a biotin molecule is coupled to them. A hybridization takes place between the target DNA sequence and the synthetic one in the case of agreement. The non-matching DNA sequences are removed by flushing the analytical surface 3.

The last step before detecting the result of analysis is to feed as marker to the analytical surface 3 so called magnetic beads 6, for example in the form of a suspension. Streptavidin molecules that couple with the biotin molecules of the synthetic DNA complements are bound to the surface of the beads 6.

Uncoupled beads 6 are subsequently removed from the analytical surface 3 by flushing. The analytical surface 3 is now prepared to such an extent that the result of analysis can be detected.

The aim of the detection is, in particular, to establish the number of beads 6 present on the analytical surface 3.

Figure 2:
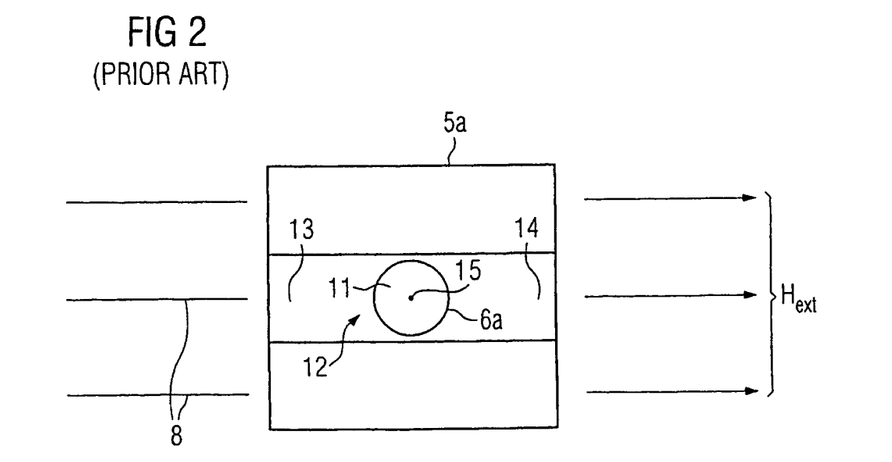
FIG. 2 shows the plan view of a known XMR sensor on which a bead is arranged centrally, approximately in the direction of the arrow II in FIG. 1.

In order to explain how the latter detection is performed according to at least one embodiment of the invention, the aim is firstly to examine the bead detection in the case of biochips in terms of the prior art corresponding to the plan view in accordance with FIG. 2, whereas FIG. 1 illustrates the general case in side view:

FIG. 2 shows a square XMR sensor 5a of a conventional biochip with an edge length of 3 μm, for example. A bead 6a with a diameter of 1 μm is to be located centrally on the XMR sensor 5a. The sensor 5a is arranged in an external magnetic field $H_{ext}$ whose field lines 8 extend parallel to the flat plane of the sensor 5a (in-plane alignment).

In the side view of the general illustration, the essentially dipolar stray field 9, caused by the external magnetic field $H_{ext}$, of a bead 6 or 6a has approximately the extent and configuration shown in FIG. 1. The stray field 9 of the bead 6 or 6a has the greater strength in the immediate vicinity of the surface of the bead 6 or 6a, and decreases rapidly with increasing distance such that the stray field is very weak at the spacing of approximately a bead diameter from the surface of the bead 6 or 6a, and can scarcely still be detected.

A spacing 10 of approximately 0.2 μm, for example, is present in FIG. 1 between the bead 6 and analytical surface 3. It results from the immobilization layer that is present between the bead 6 and the analytical region 3 and consists, for example, of the hybridized DNA molecules already mentioned further above.

According to FIG. 2, a corresponding situation results in the case of the known sensor arrangement from the plan view in accordance with the direction II of the arrow-in FIG. 1: in accordance with the prior art, sensors are arranged in such a way as to effectively prevent cross-talking of the magnet signal of the marker to a sensor further removed in the array. The spacing is selected at 20 μm such that the influence in the region of a neighboring sensor is much below one percent.

The sensor 5a sensitive to magnetic fields, which lies below the magnetic or magnetizable particle 6a, which has the function of a marker, averages the signal of the measurement-sensitive layer, since the sensor 5a is substantially wider than the marker diameter and therefore wider than the protection surface of the marker (5 μm to 0.7 μm).

It may be shown by computer simulation that in the case of an in-plane alignment in accordance with FIG. 2 the stray field 9 of the bead 6 acts only in a middle surface region 12, extending in the direction of the field lines 8 of the external field H, of the sensor 5a, the width of the surface region 12 corresponding approximately to the diameter of the bead 6a. Thus, ⅔ of the surface of the XMR sensor 5a is not even useful for detecting the particle 6a, and possibly contributes to increasing the background noise.

In the case of conventional XMR sensors 5a whose surface is greater than the diameter of a bead 6, a lesser detection sensitivity is therefore inevitably to be expected for a stray field of a bead. The stray field of the bead 6a does not have a uniform effect in the middle surface region 12. The superposition of the external field H and the stray field 9 produces a relatively slight field strengthening in the surface regions 13 and 14, which are arranged upstream and downstream, respectively, of the bead 6a with reference to the direction of the field lines 8. A field weakening results under the bead 6a, that is to say approximately in the region of its projection onto the surface of the sensor 5a. Said field weakening increases as the midpoint 15 of the projection surface 11 of the bead 6a is approached, and reaches a maximum there.

However, the sensor 5a is not capable of resolving the different field strengths or field gradients present in the middle surface region. However, it integrates over the entire middle surface region 12, field weakenings and field strengthenings being mutually compensatory. Thus, the detection capacity of a conventional sensor 5a is used overall only to a very slight extent. Consequently, the sensitivity of conventional detectors is relatively slight.

Figure 3:
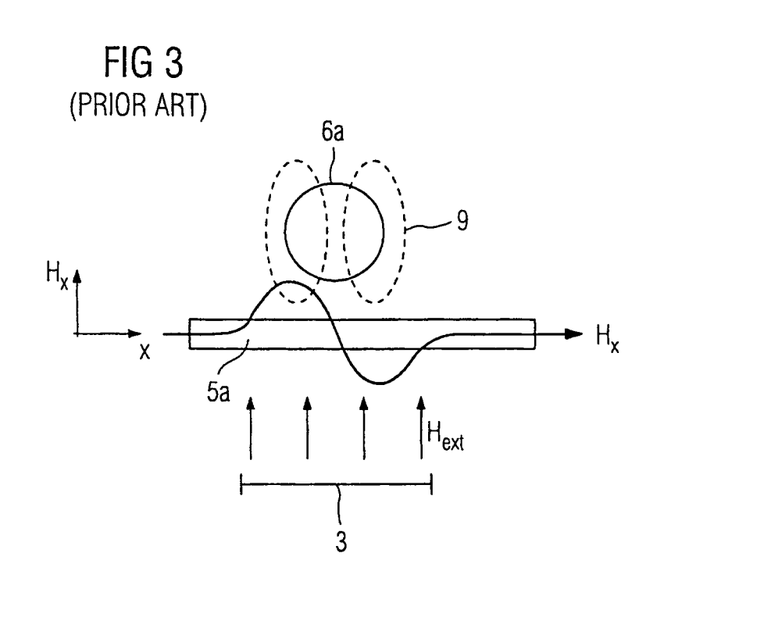
FIG. 3 shows the profile of the induced field strength in an arrangement in accordance with FIG. 2.

The latter state of affairs is illustrated in simplified fashion in FIG. 3 with an expansion of the measuring area in the x-direction according to the prior art. A large area sensor 5a and the profile of the field $H_x$ are to be seen. It is impossible to calculate the field strength $H_x$ or the marker position exactly from the sensor signal. Consequently, it is also impossible to distinguish the presence of two closely neighboring markers from only a single marker. This holds for the orthogonal field direction shown in FIG. 3 with a projection 3, and likewise for the parallel field direction from FIG. 2.

Figure 4:
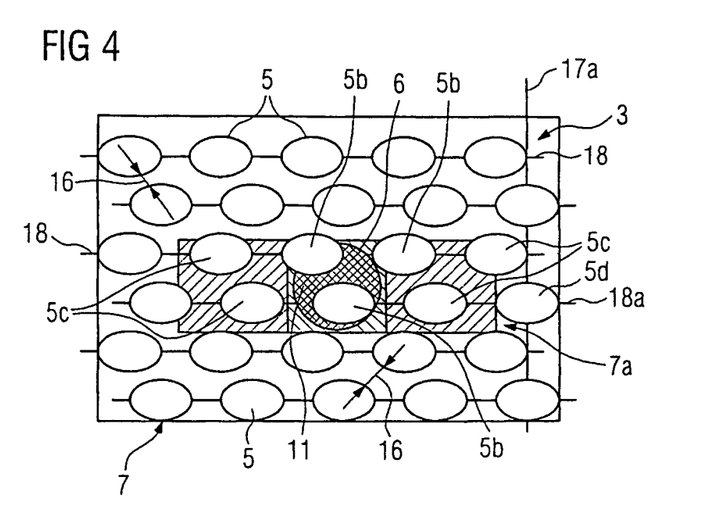
FIG. 4 shows a first design of an improved XMR sensor array.

In the case of an example embodiment of an inventive refinement in accordance with FIG. 4, the XMR sensors 5 of a sensor array 7 are smaller than the projection surface 11 of a bead 6. Moreover, the spacing 16 between the sensors 5 of a sensor array 7 is smaller than the diameter of a bead 6. Such a refinement permits an XMR sensor 5b to be arranged underneath a bead 6 or on the projection surface 11 thereof in the case of beads 6 present on the analytical surface 3. The sensor 5b is then arranged firstly in the region of the maximum of the field weakening, the latter acting in the ideal case on its total surface and consequently producing a strongly pronounced sensor signal.

It can be ensured through appropriate selection of the dimensional relationships that a sensor 5b of a group of sensors 5b, 5c—together forming a sub-array 7a—that is positioned in the region of the projection surface 11 is always located entirely inside the projection surface. A sensor array 7 of such configuration therefore has a high measuring sensitivity.

Figure 5:
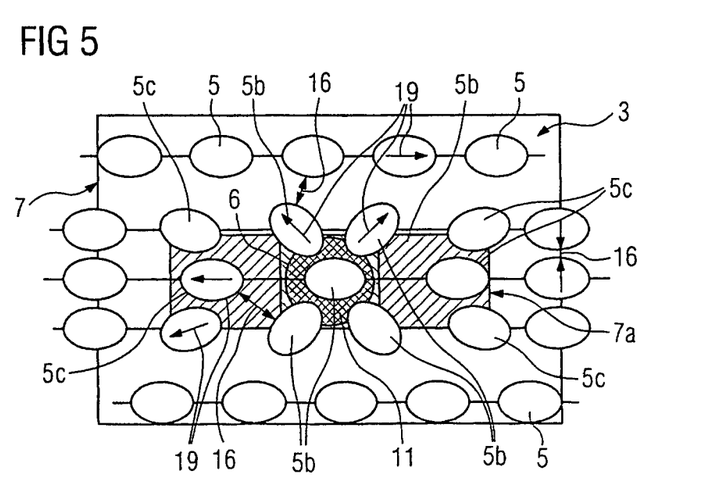
FIG. 5 shows a second design of an improved XMR sensor array.

As is to be gathered from FIGS. 4 and 5, given an occupancy of an analytical surface 3 that is not expressed completely, that is to say not expressed in the manner of a maximum density spherical packing, a few XMR sensors 5c are arranged in regions in which no field change occurs at all, or only a weak field change occurs, such as in the surface regions 13 and 14, in particular. Consequently, the sensors 5c deliver a weak signal compared with the sensors 5b. In the case of at least approximate knowledge of the field profile of a stray field emanating from a bead 6, the signals originating from the sensors 5b and 5c of a sub-array 7a can be used in order to determine the position of a bead 6 on the sensor array 7, and to detect the formation of bead clusters.

The interconnection of the XMR sensors of a sensor array 7 is performed, for example, by crossed conductor tracks 17, 18 between which the individual sensors are arranged. A few such conductor tracks are indicated in FIG. 4. 17 for example, the conductor track 17a is combined with the conductor track 18a, the XMR sensor 5b located at the intersection of the conductor tracks can thus be read out independently of the other sensors 5.

The XMR sensors $5_i$ preferably have an elliptical outline. It has emerged that such a shape yields an increased measuring sensitivity as against an approximately rectangular or square configuration. It is also advantageous in this sense when the XMR sensors $5_i$ are arranged such that their layers which are sensitive to magnetic fields and cannot be varied by an external magnetic field exhibit different directions of magnetization, which is indicated in FIG. 5 by arrows 19 in individual measuring sensors $5_i$.

The sensitivity of XMR sensors can to some extent be a function of the direction of an external magnetic field, for example as a result of the production process. The different directions of magnetization 19 of the XMR sensors prevent this effect occurring with all the sensors of a sensor array, and so the measuring sensitivity of a sensor array 7 would be greatly reduced by cumulative action.

Figure 6:
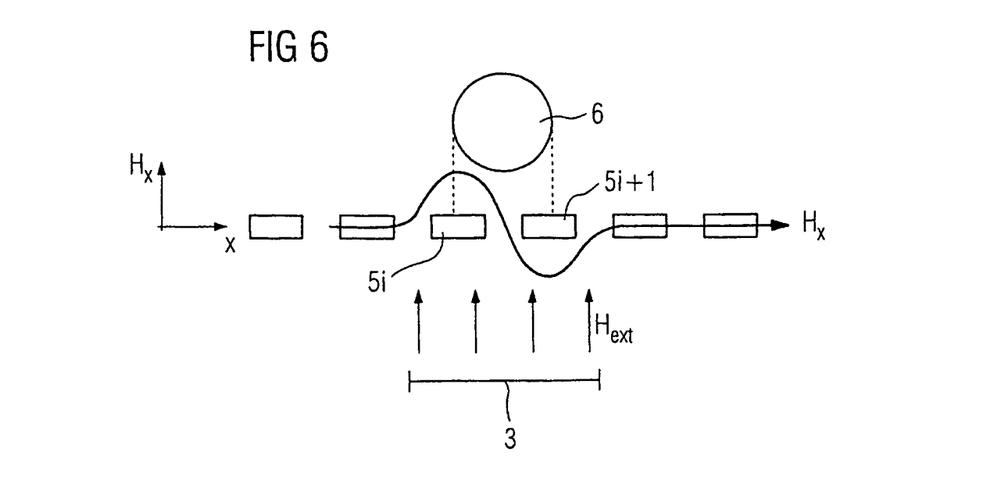
FIG. 6 shows the profile of the induced field strength in an arrangement in accordance with FIG. 4 or FIG. 5.

FIG. 6 shows a cross section of the sensor arrangement as an alternative to FIG. 4 or FIG. 5: a particle 6 is arranged above an array of sensors $5_i$ that is linear in projection. Consequently, the external magnetic field acts from below, to which end the projection surface 3 is again illustrated in addition underneath the sensor array.

In the proposed arrangement in accordance with FIG. 6, at least two sensors $5_i$ and $5_{i+1}$ lie in the region of the projection surface of the magnetic marker or bead 6. It is now possible to detect field strength gradients by separately detecting the measuring signals and offsetting them with the aid of customary mathematical methods.

The characteristic curve of sensors of the inventively used type that are sensitive to magnetic fields is defined by the magnetic materials of the ferromagnetic layers. The sensor signal is therefore a function of an applied external magnetic field $H_{ext}$. Linear sensors are fashioned such that the external magnetic field drives an operating point that is situated such that both field weakenings and field strengthenings can be detected to the same extent.

The external magnetic field in a sensor plane or the plane of the layers that are, in particular, sensitive to magnetic fields is increased in stepwise fashion in the case of hysteretic sensors with a rectangular characteristic curve. Some sensors switch earlier and some sensors switch later than unoccupied sensors owing to the influence of the bead stray field.

It is also possible, however, to use hysteretic sensors that likewise have a rectangular characteristic curve. These are designed such that the external magnetic field H orthogonal to the sensor plane triggers switching operations when stray fields are present. Demagnetized hysteretic sensors likewise having a rectangular characteristic curve have an average resistance in the original state. The switch into one of the directions of remanence in the presence of a bead stray field.

An evaluation unit of a type that can be used for TRAM-compatible evaluation of rows and columns is preferably applied as a device for reading out sensor signals. Such an evaluation is already known in principle from the prior art in the case of magnetic memories (so-called MRAMs), to which end reference is made to devices used there, which are described, for example, in detail in U.S. Pat. No. 5,852,574 A in conjunction with the MRAMS, and/or the Internet, as well, for example,: www.cs.utexas.edu/users/cart. It is therefore not the associated devices that are examined here in detail, but rather the fundamental mode of procedure according to a flowchart in accordance with FIG. 7.

In addition to the device, for evaluation, an electronic evaluation unit further has a sense amplifier for linear sensors and optionally a TRAM sense amplifier for digital sensors. Also provided are memories for the values of the individual signals of the XMR sensors $5_i$ of a sensor array 7.

The calculations of the position of individual beads is performed with the aid of an arithmetic logic unit that evaluates the separate measuring signals of the individual sensors 5'.

Figure 7:
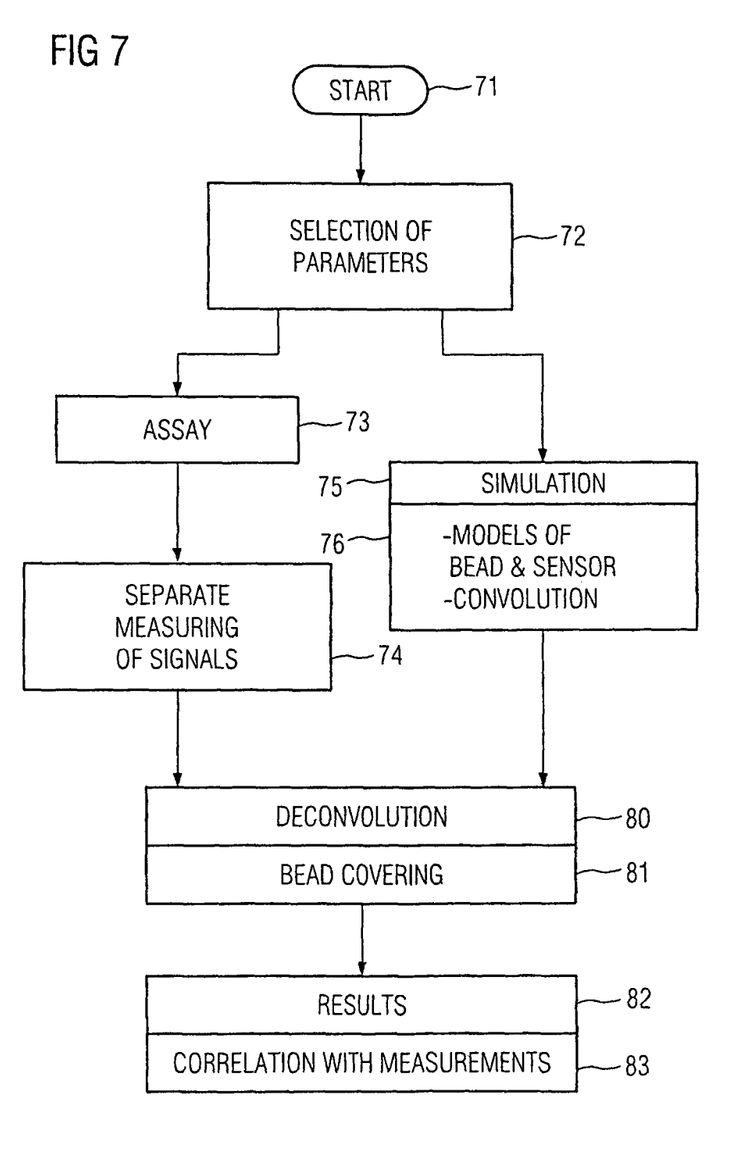
FIG. 7 shows a flowchart of the mode of procedure in the field calculation for FIG. 4 or FIG. 5.

The computational procedure is explained with the aid of FIG. 7: after the initialization at start 71, the unit 72 selects parameters in accordance with the present biological problem.

An operating method is performed, or the assay is conducted with the aid of the setpoint inputs of the unit 73. In accordance with method stage 74, the signals of the individual sensors are detected separately in the process and are stored with the assignment to the array.

Parallel thereto, a simulation that is performed in a computer as computer simulation using a program is carried out in unit 75: to this end, models of the beads and of the sensors are generated and combined with one another in unit 76: all signal combinations such as could point to the presence of a bead are generated by way of mathematical convolution methods.

A deconvolution of the data is performed at stage 80. The bead occupancy can be determined therefrom in unit 81. Consequently, unit 82 specifies the reproduction or output of the occupancy of the sensors with the magnetic markers, that is to say the beads 6. The correlation with the measurement is subsequently confirmed in unit 83, after which the evaluation is terminated.

A device for carrying out the above method, in at least one embodiment, requires a drive circuit for setting the field strength of the external magnetic field and reading out the entire array as well as calculating and outputting the distribution of the sub-array, which is designed in the usual way.

An embodiment of the invention was explained above with particular reference to an example of a biochip. However, it is valid in the same way for general magnetic sensors within the field of technical applications where, for example, weak magnetic fields are to be precisely localized and characterized. In addition to the marking of objects, for example dusts, mention was also made of the need for direct characterization of magnetic microparticles, for example during analysis of corrosion products in oils.

The magnetic field detector described also achieves this in such applications with the aid of the magnetic field sensors arranged in a geometrically suitable fashion, and of an improved area ratio by virtue of the fact that means for field strengthening and for field weakening are likewise provided, and both the maximum field strengthening and field weakening are likewise detected.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for measuring a local magnetic field, comprising:
   providing, in a region of the magnetic field, an arrangement of magnetic field sensors in an array, each of the sensors including at least one layer sensitive to magnetic fields;
   arranging a sensor matrix, including a number of the magnetic field sensors, at least in a subregion of a measuring area of the field;
   configuring dimensions of the magnetic field sensors, dimensions of the layer sensitive to the magnetic fields, and grid dimension of the sensor matrix such that at least two of the sensors are influenced by the local magnetic field;
   generating the local magnetic field by at least one of magnetic and magnetizable particles, whereby a stray field of the particles are actable upon at least two magnetic field sensors;
   reading a measured signal of each of the magnetic field sensor separately and independently of other sensor signals; and
   determining a position of a magnetizable particle by determining a magnetic field distribution from the measured signals of the individual magnetic field sensors by offsetting the separately and independently read sensor signals and a known spatial distribution of the magnetic field sensors.

2. The method as claimed in claim 1, wherein XMR sensors are used as the magnetic field sensors.

3. The method as claimed in claim 2, wherein an analytical surface is assigned a sensor array of XMR sensors, and wherein the surface of the XMR sensors and a mutual spacing of neighboring sensors are configured such that the surface is smaller than a projection surface of at least one of the magnetic and magnetizable particles, and the mutual spacing of the sensors is smaller than the diameter of a magnetizable particle on the sensor array.

4. The method as claimed in claim 2, wherein the XMR sensors are at least one of GMR and TMR sensors.

5. The method as claimed in claim 1 further comprising using a linear array of sensors.

6. The method as claimed in claim 5, wherein the sensor matrix arrangement in the array is configured such that a particle influences a sub-array of a plurality of sensors.

7. The method as claimed in claim 1, wherein a two-dimensional array is used as part of a prescribed matrix arrangement.

8. The method as claimed in claim 7, wherein the stray field is detected by particles with a diameter of 0.5 μm to 2 μm.

9. The method as claimed in claim 1, wherein the offsetting is performed by using mathematical convolution/deconvolution methods.

10. The method as claimed in claim 1, wherein a computer simulation is performed.

11. The method as claimed in claim 1, wherein possible particle occupancies are determined and selected via a comparison between the measured signals and a simulated model of beads and sensors.

12. The method as claimed in claim 1, wherein a spacing of neighboring sensors is smaller than a diameter of a magnetizable particle on the sensor array.

13. The method as claimed in claim 1, wherein the method is applied in biotechnology by using magnetic beads as the at least one of magnetic and magnetizable particles.

14. The method as claimed in 13, wherein a result of analysis carried out on the analytical surface of a biochip is read by detecting the magnetic beads.

15. The method as claimed in claim 14, wherein the method is applied to DNA analysis via biochips.

16. The method as claimed in claim 4, wherein the method is applied to protein analysis via biochips.

17. The method as claimed in claim 13, wherein the method is applied to DNA analysis via biochips.

18. The method as claimed in claim 13, wherein the method is applied to protein analysis via biochips.

19. The method as claimed in claim 1 for use in biotechnology, the method further comprising:
   arranging the magnetic field sensor, with at least one layer sensitive to magnetic fields underneath the analytical surface;
   immobilizing a number of magnetic beads in the analytic region based on a biologic parameter;
   configuring dimensions of the magnetic field sensors, the dimensions of the layer sensitive to magnetic fields, and the grid dimension of the sensor matrix in such a way that at least two sensors are influenced by the local stray field of the magnetic beads; and
   reading the measured signal of each magnetic field sensor separately, the magnetic field distribution being determined from the measured signals of the individual magnetic field sensors by offsetting the separately read sensor signals and the known spatial distribution of the magnetic field sensors.

20. A device for characterizing a local magnetic field, comprising:
   a sensor area including a number of magnetic field sensors that, in each case, include at least one layer sensitive to magnetic fields and are interconnected via cross-conductors for reading out a signal of each sensor independently of other sensors, a size of the magnetic field sensors and a surface of the at least one layer sensitive to the magnetic fields and the grid dimension of the sensors are configured such that at least two neighboring sensors are influenced by local stray field of at least one of a magnetic magnetizable particle and a magnetic bead.

21. The device as claimed in claim 20, wherein the device is a biochip and includes an analytical surface and a sensor array of XMR sensors, the sensor array being arranged in a region of the analytical surface.

22. The device as claimed in claim 21, wherein a surface of the XMR sensors and a mutual spacing of neighboring sensors are smaller than 2 μm.

23. The device as claimed in claim 21, wherein at least some of the XMR sensors are designed to detect a field strengthening and a field weakening.

24. The device as claimed in claim 21, wherein at least some of the XMR sensors are designed to detect a field strengthening and a field weakening.

25. The device as claimed in claim 21, wherein a two-dimensional array with a prescribed matrix arrangement of the XMR sensors is used as the sensor area.

26. The device as claimed in claim 25, wherein the matrix arrangement is an array and is configured such that individual XMR sensors have a smaller surface than a projection of the magnetic beads.

27. The device as claimed in claim 26, wherein a spacing of the individual XMR sensors is smaller than at least one of a magnetic bead and a projection thereof onto the sensor surface.

28. The device as claimed in claim 21, wherein the XMR sensors have an oval outline.

29. The device as claimed in claim 21, wherein the XMR sensors are GMR sensors.

30. The device as claimed in claim 21, wherein the XMR sensors are TMR sensors.

31. The device as claimed in claim 20, wherein the sensor area includes a linear array.

32. A method for measuring a local magnetic field, comprising:

provinding, in a region of the magnetic field, an arrangement of magnetic field sensors in an array, each of the sensors including at least one layer sensitive to magnetic fields;

arranging a sensor matrix, including a number of the magnetic field sensors, at least in a sub-region of a measuring area of the field;

configuring dimensions of the magnetic field sensors, dimensions of the layer sensitive to the magnetic fields, and grid dimension of the sensor matrix such that at least two of the sensors are influenced by the local magnetic field;

generating the local magnetic field by at least one of magnetic and magnetizable particles, wherein a spacing of neighboring sensors is smaller than a diameter of a particle such that a stray field of the particles are actable upon at least two magnetic field sensors;

reading a measured signal of each of the magnetic field sensor separately and independently of other sensor signals; and determining a position of a magnetizable particle by determining a magnetic field distribution from the measured signals of at least two neighboring magnetic field sensors by offsetting the separately and independently read sensor signals and a known spatial distribution of the magnetic field sensors.

* * * * *